United States Patent [19]
An et al.

[11] Patent Number: 6,103,528
[45] Date of Patent: Aug. 15, 2000

[54] REVERSIBLE GELLING CULTURE MEDIA FOR IN-VITRO CELL CULTURE IN THREE-DIMENSIONAL MATRICES

[75] Inventors: Yuehuei H. An, Charleston; Vladimir A. Mironov, Mt. Pleasant, both of S.C.; Anna Gutowska, Richland, Wash.

[73] Assignees: Battelle Memorial Institute, Richland, Wash.; Medical University of South Carolina, Charleston, S.C.

[21] Appl. No.: 09/062,483

[22] Filed: Apr. 17, 1998

[51] Int. Cl.[7] .............................. C12N 5/06; C12N 5/08; C12N 11/04

[52] U.S. Cl. .................. 435/395; 424/93.7; 435/182; 435/396; 435/397; 435/404

[58] Field of Search .................................... 435/174, 177, 435/180, 182, 243, 253.6, 252.1, 255.21, 395, 396, 397, 404, 405; 424/93.7

[56] References Cited

U.S. PATENT DOCUMENTS 5,709,854  1/1998  Griffith-Cima et al. ............... 424/93.7

OTHER PUBLICATIONS

Treatment of Deep Cartilage Defects in the Knee with Autologous Chondrocyte Transplantation, M Brittberg et al., N Engl J Med, 1994, Oct. 6: 331(14): 889–895.

Development of a Tissue Analog for Cartilage Repair, J.M. Pachence, S.R. Frenkel, and J. Lin, Mat. Res. Soc. Symp. Proc. vol. 252, 1992.

Chondrocytes Embedded in Collagen Gels Maintain Cartilage Phenotype During Long Term Cultures, T Kimura, N Yasui, S Ohsawa, K Ono.

53 Biomaterials Involved in Cartilaginous Implants, Z. Nevo, D. Robinson, D.G. Mendes, N. Halperin, *Biomaterials Science*, Eds: BD Rafner et al., Academic Press 1996.

Dedifferentiated Chondrocytes Reexpress the Differentiated Collagen Phenotype When Cultured in Agarose Gels, PD Benya, JD Schaffer, Cell 1982, Aug: 30(1): 215–224.

Enhanced Tumor Growth of Both Primary and Established Human and Murine Tumor Cells . . . , R Fridman, et al., J Natl Cancer Inst 1991 Jun. 5: 83(11): 769–774.

Fibroblast Growth Factor Stimulated Colony Formation of Differentiated Chondrocytes in Soft Agar, Y. Kato, et al., J Cell Physiol 1987, Dec. 133(3): 491–498.

Phenotype and Biological Activity of Neonatal Equine Chondrocytes Cultured in a . . . , DA Hendrickson, AJ Nixon, HN Erb, G Lust, Am J Vet Res 1994, Mar, 55(3): 510–414.

Phenotype Stability of Bovine Articular Chondrocytes After Long–Term Culture in Alginate Beads, HJ Hauselmann, RJ Fernandez, SS Mok, TM Schmid, JA Block, MB Aydelotte, KE Kuettner, EJ Thonar, J Cell Sci, 1994, Jan: 107(Pt 1): 17–27.

Injectable Cartilage Using Thermosensitive Polymers: A Potential Method for Nipple Reconstruction, YI Cao et al., Tissue Engineering Society, Dec. 12, 1996, Orlando, Fl.

Fate of Injectable Chondrocyte/Polymer Constructs in Immunocompetent Animal, SK Ashiku et al., Tissue Engineering Society, Dec. 13–15, 1996, Orlando, FL.

Thermally Reversible Polymer Gels For Biohybrid Artifical Pancreas, B Vernon, A Gutowska, SW Kim, YH Bae, Macromal. Symp. 109, 155–167, Jun. 12, 1996.

*Primary Examiner*—David M. Naff
*Attorney, Agent, or Firm*—Paul W. Zimmerman

[57] ABSTRACT

A gelling cell culture medium useful for forming a three dimensional matrix for cell culture in vitro is prepared by copolymerizing an acrylamide derivative with a hydrophilic comonomer to form a reversible (preferably thermally reversible) gelling linear random copolymer in the form of a plurality of linear chains having a plurality of molecular weights greater than or equal to a minimum gelling molecular weight cutoff, mixing the copolymer with an aqueous solvent to form a reversible gelling solution and adding a cell culture medium to the gelling solution to form the gelling cell culture medium. Cells such as chondrocytes or hepatocytes are added to the culture medium to form a seeded culture medium, and temperature of the medium is raised to gel the seeded culture medium and form a three dimensional matrix containing the cells. After propagating the cells in the matrix, the cells may be recovered by lowering the temperature to dissolve the matrix and centrifuging.

47 Claims, 1 Drawing Sheet

REVERSIBLE GELLING CULTURE MEDIA FOR IN-VITRO CELL CULTURE IN THREE-DIMENSIONAL MATRICES

This invention was made with Government support under Contract DE-AC06-76RLO 1830 awarded by the U.S. Department of Energy. The Government has certain rights in the invention.

FIELD OF THE INVENTION

The present invention relates generally to a reversible gelling cell culture media and method of making same. More specifically, the gelling cell culture media is a combination of a random copolymer of an [meth-]acrylamide derivative with a hydrophilic comonomer combined with a cell culture media. As used herein, the term [meth-]acrylamide denotes methacrylamide, acrylamide, or combinations thereof.

BACKGROUND OF THE INVENTION

Three dimensional cell matrices are used in tissue engineering and biotechnology for in-vitro and in-vivo cell culturing. For example, the paper TREATMENT OF DEEP CARTILAGE DEFECTS IN THE KNEE WITH AUTOLOGOUS CHONDROCYTE TRANSPLANTATION, M Brittberg, A Lindahl, A Nilsson, C Ohlsson, O Isaksson, L Peterson, N Engl J Med, Oct. 6, 1994: 331(14): 889–895 reports successful transplantation of healthy knee cartilage. The transplant was accomplished by obtaining healthy knee chondrocytes, culturing them in the laboratory for 14–21 days then injecting the cultured chondrocytes to the damaged area. The culturing method is typically monolayer or planar culturing as described, for example in the paper DEVELOPMENT OF A TISSUE ANALOG FOR CARTILAGE REPAIR, J. M. Pachence, S. R. Frenkel, and J. Lin, Mat. Res. Soc. Symp. Proc. Vol. 252, 1992, discusses culturing cells (chondrocytes) on a planar substrate and harvesting them for placement. In this paper, instead of direct in-vivo injection, placement was into a three dimensional solid scaffold of collagen. Nevertheless, the monolayer culturing was the same which turns cultured cells to undesirable "fibroblast-like cells".

Another paper, CHONDROCYTES EMBEDDED IN COLLAGEN GELS MAINTAIN CARTILAGE PHENOTYPE DURING LONG TERM CULTURES, T Kimura, N Yasui, S Ohsawa, K Ono, discusses successful chondrocyte phenotype in-vitro maintenance in a collagen gel. However, no discussion of cell recovery suggests that collagen gel is useful solely as a cell carrier for implantation or for studying cell function, but not for in-vitro propagation.

The book chapter 53 BIOMATERIALS INVOLVED IN CARTILAGINOUS IMPLANTS, Z. Nevo, D. Robinson, D. G. Mendes, N. Halperin, in the book *Biomaterials Science*, Eds: B D Rafner, A S Hoffman, F J Schoen, J E Lemons, Academic Press 1996 discusses using a hyaluronic-acid based adhesive gel embedded with chondrocyte cell culture in-vivo. The chapter further discusses collagen based scaffolds and identifies the limitation that the cells tend to grow mainly on the surface of the collagen scaffold because of lack of nourishment of more deeply situated cells. Polylactide and polyglycolide matrices are also discussed concluding that further investigation is needed. These bioabsorbable materials are solely used as scaffolds for cell seeding and later implantation with no discussion of in-vitro propagation or recovery of cells from the scaffolds.

Gelling three dimensional matrices have also been investigated as reported in DEDIFFERENTIATED CHONDROCYTES REEXPRESS THE DIFFERENTIATED COLLAGEN PHENOTYPE WHEN CULTURED IN AGAROSE GELS, P D Benya, J D Shaffer, Cell Aug. 30, 1982 (1): 215–224. Agarose culture is a method to maintain chondrocyte phenotype in a three dimensional matrix. However, the cells in agarose are not readily recoverable. Agarose may be liquefied by heating to 80° C., but that overheats the cells and the cells do not survive. Alternatively, the agarose may be degraded with the enzyme agarase. However, the effect of the agarase is insufficient to readily dissolve the bulk gel and collect the cells.

Another gelling three-dimensional cell matrix has the trade name Matrigel which is naturally produced by tumor cells. Enzymatic action is required for dissolution or degradation of the gel which, again damages any cells therein. Because Matrigel is a tumor cell product, it is used primarily for in-vivo promotion of tumor cell growth for mice studies as exemplified in the paper ENHANCED TUMOR GROWTH OF BOTH PRIMARY AND ESTABLISHED HUMAN AND MURINE TUMOR CELLS IN ATHYMIC MICE AFTER COINJECTION WITH MATRIGEL, R Fridman, M C Kibbey, L S Royce, M Zain, M Sweeney, D L D L Jicha, J R Yannelli, G R Martin, H K Kleinman, J Natl Cancer Inst Jun. 5, 1991: 83(11): 769–774.

The paper FIBROBLAST GROWTH FACTOR STIMULATED COLONY FORMATION OF DIFFERENTIATED CHONDROCYTES IN SOFT AGAR, Y Kato, M Iwamoto, T Koike, J Cell Physol December 1987: 133(3): 491–498, discusses a soft agar as a three dimensional cell matrix wherein the fibroblast growth factor selectively stimulates growth of differentiated chondrocytes in-vitro. It is believed that cells are not easily recovered from soft agar, therefore, making soft agar useful for studying cell function but not useful for in-vitro cell propagation for subsequent implantation.

The paper PHENOTYPE AND BIOLOGICAL ACTIVITY OF NEONATAL EQUINE CHONDROCYTES CULTURED IN A THREE-DIMENSIONAL FIBRIN MATRIX, D A Hendrickson, A J Nixon, H N Erb, G Lust, Am J Vet Res March 1994, 55(3): 410–414, discusses using a3D culture in fibrin to study the differentiation and function of embedded chondrocytes. Because fibrin can not be readily dissolved by any means to release the embedded cells, fibrin is not a candidate for in-vitro cell propagation.

The paper PHENOTYPE STABILITY OF BOVINE ARTICULAR CHONDROCYTES AFTER LONG-TERM CULTURE IN ALGINATE BEADS, H J Hauselmann, R J Fernandez, S S Mok, T M Schmid, J A Block, M B Aydelotte, K E Kuettner, E J Thonar, J Cell Sci, January 1994: 107(Pt 1): 17–27, reports chondrocyte phenotype stability with the ability to recover cells by chelating the calcium. Although useful either as a carrier for cell implantation or for studying cell function or behavior, alginate beads are not attractive for in-vitro propagation because of the additional steps of chelation and separation of cells from the chelator.

Use of a reverse thermosensitive polymer has been demonstrated for in-vivo cartilage formation. The reverse thermosensitive polymer was Pluronics, a co-polymer of polyethylene oxide and polypropylene oxide which is biodegradable, biocompatible, exists as a liquid at room temperature and polymerizes to a thick gel when exposed to physiologic temperature (body temperature). This work has been reported in two abstracts (1) INJECTABLE CARTILAGE USING THERMOSENSITIVE POLYMERS: A POTENTIAL METHOD FOR NIPPLE RECONSTRUCTION, Y I Cao, C Peetz, K Tran, C A Vacanti, Tissue Engineering Society, Dec. 12–13, 1996, Orlando, Fla., and (2) FATE OF INJECTABLE CHONDROCYTE/POLYMER CONSTRUCTS IN IMMUNOCOMPETENT ANIMAL, S K Ashiku, M A Randolph, D J Mathisen, M J Yaremchuk, C A Vacanti, Tissue Engineering Society, Dec. 13–15, 1996, Orlando, Fla. Although used for implantation, the Pluronics material was not used for in-vitro cell propagation. Disadvantages include the high concentration of the Pluronics material (30–40% w/v) and possibly difficult recovery.

In spite of the forgoing research, the standard method of cell implantation is by propagation in a monolayer culture followed by injection. Until the present invention, there has simply not been a sufficiently reliable method of 3D cell-seeding and recoverable in-vitro propagation for cell propagation.

Accordingly, there is a need in the field of three dimensional cell matrices for a three dimensional cell matrix useful for in-vitro cell propagation from which the cells may be separated without damage, without added compounds (e.g. chelator), and without excessive amount of matrix material to be removed, wherein phenotypical cells may be recovered with their original phenotype and subsequently used for cell seeding and implantation.

SUMMARY OF THE INVENTION

The present invention is a combination of a thermally reversible gel or thermally reversible gelling copolymer that is a random copolymer of an [meth-]acrylamide derivative and a hydrophilic comonomer, wherein the random copolymer is in the form of a plurality of linear chains having a plurality of molecular weights greater than or equal to a minimum gelling molecular weight cutoff, combined with a cell culture media. Growth factors may also be added to the gelling cell culture media.

The method of the present invention for making a gelling cell culture media has the steps of:
  (a) making a thermally reversible gelling copolymer by
    (i) mixing an [meth-]acrylamide derivative with a hydrophilic comonomer in a solvent with an initiator forming a reaction mixture;
    (ii) polymerizing the reaction mixture and forming a first random copolymer having a plurality of linear chains having a plurality of molecular weights;
    (iii) purifying the polymerized first random copolymer and obtaining a second random copolymer having a plurality of molecular weights greater than or equal to a minimum gelling molecular weight cutoff; and
  (b) mixing a cell culture media with the thermally reversible gelling copolymer to obtain the gelling cell culture media. The gelling cell culture media may be further provided with cells then gelled by raising the temperature to a body temperature of about 37° C. The gelling cell culture media may be further enhanced by combining the thermally reversible gelling copolymer with one or more growth factor(s).

Seeding phenotype cells (e.g. chondrocytes) to a scaffold is useful to the present methods of using morphologically fibroblast-like chondrocytes.

Advantages of the present invention include (1) the thermally reversible gel of the present invention exhibits a thermodynamic stability, and when gelled, will not reverse to the liquid state upon dilution but may reverse to the liquid state only in response to a temperature change. Moreover, the thermally reversible gel of the present invention in a solution state has lower initial viscosity more suitable for cell culture media and cell mixing. A distinct advantage of the present invention over the present methods of making three dimensional gelling cell matrices is the ability to recover a substantial fraction of live cells because the temperature to fluidize the gelled cell culture media is about room temperature or below a body temperature that permits the cells to survive while the fluidized cell culture media is removed. This advantage is facilitated by the amount of solvent to polymer being greater than 70 wt %.

Conversely, the amount of the polymer is less than 30 wt %, preferably less than 20 wt % most preferably less than 5 wt %. Further advantages include propagating cells (especially cells having different phenotypes including but not limited to chondrocytes, hepatocytes, stem cells and combinations thereof) before in-vivo implantation or for in-vitro studies of cell function or treatment wherein cell phenotype is maintained. Implantation of chondrocytes, hepatocytes, or other phenotypical cells with their original phenotype is desirable, having the advantages of faster and more direct tissue repair and/or secretion of useful factors (such as growth factors).

It is an object of the present invention to provide a cell culture media useful as a three-dimensional cell matrix from which live cells may be recovered.

It is a further object of the present invention wherein the cells are phenotypical cells that are recovered with their original phenotype.

The subject matter of the present invention is particularly pointed out and distinctly claimed in the concluding portion of this specification. However, both the organization and method of operation, together with further advantages and objects thereof, may best be understood by reference to the following description taken in connection with accompanying drawings wherein like reference characters refer to like elements.

DESCRIPTION OF THE PREFERRED EMBODIMENT(S)

The present invention uses a thermally reversible copolymer that is useful as a gel that forms without substantial syneresis when the thermally reversible copolymer is in an aqueous solution. Syneresis is defined as water expelled from a copolymer matrix upon gelation. Substantial syneresis is more than about 10 wt % water expelled from the copolymer matrix. According to the present invention, it is preferred that the syneresis be less than about 10 wt %, more preferably less than about 5 wt % and most preferably less than about 2 wt %. Substantially no syneresis is syneresis of less than about 2 wt %, preferably 0 wt %.

Figure 1:
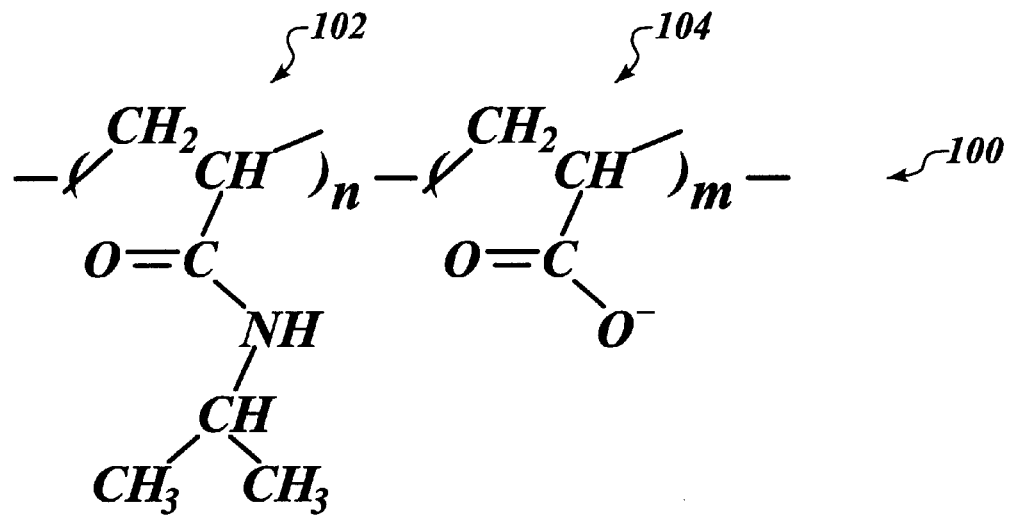
FIG. 1 is a depiction of a random copolymer of poly(N-isopropylacrylamide-co-acrylic acid) (NiPAAm/AAc), where n and m denote sequences of NiPAAm and AAc (respectively) that are of random length and are randomly distributed along the copolymer chain.

The thermally reversible copolymer is a linear random copolymer of an [meth-]acrylamide derivative and a hydrophilic comonomer wherein the linear random copolymer is in the form of a plurality of linear chains having a plurality of molecular weights greater than or equal to a minimum gelling molecular weight cutoff. According to the present invention, the minimum gelling molecular weight cutoff is at least several thousand and is preferably about 12,000. The presence of a substantial amount of copolymer or polymer chains having molecular weights less than the minimum gelling molecular weight cutoff results in a milky solution that does not gel. Further, the amount of hydrophilic comonomer in the linear random copolymer is preferably less than about 10 mol %, more preferably less than about 5 mol% and most preferably about 2 mol%. The structure of linear chains is not cross-linked. Moreover, the linear random copolymer structure is one in which a linear chain 100 is shared by randomly alternating portions of the [meth-]acrylamide derivative 102 and the hydrophilic comonomer 104 as depicted in FIG. 1.

The [meth-]acrylamide derivative is an N,N'-alkyl substituted [meth-]acrylamide including but not limited to N-isopropyl[meth-]acrylamide, N,N'-diethyl[meth-]acrylamide, N-[meth-]acryloylpyrrolidine, N-ethyl[meth-]acrylamide, and combinations thereof.

The hydrophilic comonomer is any hydrophilic comonomer that co-polymerizes with the [meth-]acrylamide derivative. Preferred hydrophilic comonomers are hydrophilic [meth-]acryl- compounds including but not limited to carboxylic acids, [meth-]acrylamide, hydrophilic [meth-]acrylamide derivatives, hydrophilic [meth-]acrylic acid esters. The carboxylic acid may be, for example, acrylic acid, methacrylic acid and combinations thereof. The hydrophilic acrylamide derivatives include but are not limited to N,N-diethyl[meth-]acrylamide, 2-[N,N-dimethylamino]ethyl[meth-]acrylamide, 2-[N,N-diethylamino]ethyl[meth-]acrylamide, or combinations thereof. The hydrophilic [meth-]acrylic esters include but are not limited to 2-[N,N-diethylamino]ethyl[meth-]acrylate, 2-[N,N-dimethylamino]ethyl[meth-]acrylate, and combinations thereof.

According to the present invention, the thermally reversible polymer may be mixed with an aqueous solvent to form a thermally reversible gelling solution or reversible gelling solution. The aqueous solvent includes but is not limited to water and aqueous salt solutions. The salt solution is preferably a phosphate buffered saline solution for medical use.

The thermally reversible gelling solution is further combined with a cell culture medium to form the gelling cell culture medium of the present invention. The cell culture medium may be any cell culture media including but not limited to RPMI-1640 medium, DMEM (Dulbecco's Modified Eagle's Medium), and combinations thereof. In addition, fetal bovine serum may be added to the cell culture medium.

The method of making the gelling cell culture medium according to the present invention has the steps of:
(a) making a thermally reversible polymer by
  (i) mixing an [meth-]acrylamide derivative with a hydrophilic comonomer in a reaction solvent with an initiator forming a reaction mixture;
  (ii) polymerizing the reaction mixture and forming a first linear random copolymer having a plurality of linear chains having a plurality of molecular weights;
  (iii) isolating and purifying the polymerized first linear random copolymer and obtaining a second linear random copolymer having a plurality of molecular weights greater than or equal to a minimum gelling molecular weight cutoff; and
(b) mixing the thermally reversible gelling solution with a cell culture medium to obtain the gelling cell culture medium.

The alternatives for the [meth-]acrylamide derivative and the hydrophilic comonomer have been set forth above and are not repeated here.

The reaction solvent may be aqueous or non-aqueous. The preferred aqueous solvent is simply water. Alternatively, the aqueous solvent is a salt solution. The non-aqueous solvent may be a hydrocarbon including but not limited to oxygenated hydrocarbon solvent, for example dioxane, chlorinated hydrocarbon solvent, for example chloroform, an aromatic hydrocarbon, for example benzene. Precipitation of the polymer occurs during polymerization in benzene. Dioxane is the preferred solvent because there is no precipitation during copolymerization thereby imparting greater uniformity of composition of the random copolymer (NiPAAM/AAc).

The amount of aqueous solvent with respect to [meth-]acrylamide derivative is preferably about 80 wt %, but may range from about 30 wt % to about 98 wt %. The amount of non-aqueous solvent with respect to the [meth-]acrylamide derivative is preferably about 80 wt % but may range from about 30 wt % to about 98 wt %.

The initiator may be any free radical initiator compatible with the [meth-]acrylamide derivative. The preferred initiator is 2,2'-azobis-isobutyrolnitrile (AIBN).

The amount of the initiator with respect to the reaction mixture of solvent and polymer is preferably about 0.1 wt % but may range from about 0.01 wt % to about 2 wt %.

A reversible gelling solution is made by mixing the thermally reversible polymer with an aqueous solution. The amount of aqueous solution with respect to polymer is from about 70 wt % to about 99 wt %, preferably greater than 70 wt %, most preferably about 98 wt %. for NiPAAm/AAc to achieve a nonresorbable reversible gel with substantially no syneresis. Conversely, the amount of the polymer is less than 30 wt %, preferably less than about 10 wt % and most preferably less than about 5 wt %. The aqueous solution is preferably a salt solution.

The method of the present invention further includes the steps of placing live cells into the gelling cell culture medium as a seeded gelling cell culture medium, and raising the temperature of the seeded gelling cell culture medium and forming a three-dimensional cell seeded gelled solid matrix. More specifically, the preferred steps of obtaining the three-dimensional cell seeded gelled solid matrix are:

(a) prepare a 10 wt % polymer solution in deionized water. The polymer dissolves faster in a cool solution. An external ice bath or 4° C. refrigerator may be used. Magnetic stirring or slow rotation is needed. Avoid vigorous shaking or stirring that would cause foaming.

(b) Sterilize the polymer solution for 30 minutes in an autoclave. Cover the container or flask containing the polymer. The polymer will gel and will need to be re-dissolved by cooling to a completely clear state.

(c) Combine the sterilized polymer solution with an equal amount of cell culture medium, complete 2× DMEM, so that the final polymer concentration is not less than 5 wt % as a gelling cell culture medium.

(d) Add the gelling cell culture medium to cells and mix thoroughly to insure that the cells are substantially evenly suspended as a cell seeded gelling medium.

(e) Heat the cell seeded gelling medium to about 37° C. to make a three dimensional matrix. Wait for complete gelation whereupon the appearance will be white and opaque and will not flow if tilted. Temperature must be maintained to avoid dissolution.

(f) After gelation, additional medium may be added onto the three dimensional matrix. The additional medium must be pre-heated, preferably to about 38° C. to avoid dissolving the three dimensional matrix.

(g) Cells may be recovered by cooling the three dimensional matrix below 37° C., for example room temperature then centrifuging. Cells may be further washed with phosphate buffered saline for complete removal of any remaining gelling cell culture medium.

EXAMPLE 1

An experiment was conducted to demonstrate synthesis and thermoreversible gel formation of poly(N-isopropylacrylamide-co-acrylic acid)(NiPAAm/AAc). The linear high molecular weight NiPAAm/AAc copolymers containing different amounts of AAc were synthesized by a free radical copolymerization.

The [meth-]acrylamide derivative was N-isopropylacrylamide (NiPAAm) (Fisher, Co.) that was recrystallized from hexane before use. The initiator 2,2'-azobis-isobutyronitrile (AIBN) (Eastman Kodak, Co.) was recrystallized from methanol. The hydrophilic comonomer was acrylic acid (AAc) (Aldrich Co.) that was purified before use by vacuum distillation at 39° C./10 mmHg. The reaction solvent, dioxane, HPLC grade (Aldrich Co.) was used as received. The mixture of [meth-]acrylamide derivative, initiator, hydrophilic comonomer, and solvent formed the reaction mixture.

The molar feed ratio of NiPAAm to AAc was varied as 99:1, 98:2 and 97:3. The copolymerization was carried out in dioxane (80 wt %), with the amount of AIBN initiator of $1.219 \times 10^{-3}$ mols/L. The reaction proceeded at 60° C. for 18 hours. The resulting copolymer solution was diluted with fresh dioxane and added dropwise to a ten-fold excess of diethyl ether producing copolymer precipitation. The precipitated copolymer was isolated by filtration and drying. The isolated copolymer was redissolved in acetone and reprecipitated into ten-fold excess diethyl ether. The final, essential step of purification involved dialysis of aqueous copolymer solution through 12,000–14,000 molecular weight cut off (MWCO) dialysis membrane. Dialysis removed the residual unreacted monomer and all copolymer fractions with molecular weights smaller than the MWCO of the dialysis membrane, resulting in a purified copolymer product. The purified copolymer product was further freeze dried.

The removal of molecular weights below 12,000 from the synthesized copolymers was confirmed by gel permeation chromatography. The removal of unreacted monomers was confirmed by nuclear magnetic resonance.

The lower critical solution temperature (LCST) of the synthesized copolymers was evaluated by the cloud point determination method. In this method, 1 wt % solutions of synthesized copolymers in phosphate buffered saline were heated from 20 to 50° C. in 2-deg increments every 10 min. and the absorbance at 450 nm was measured. The cloud point, corresponding to the LCST was determined as the temperature at the inflection point in the absorbance versus temperature curve. NiPAAm homopolymer exhibited an LCST at 32° C. Copolymerization with hydrophilic comonomers shifted the LCST to the physiological temperature range of 36–38° C. NiPAAm/AAc copolymer containing 2 mol % of AAc exhibited the LCST at 37° C.

Figure 2:
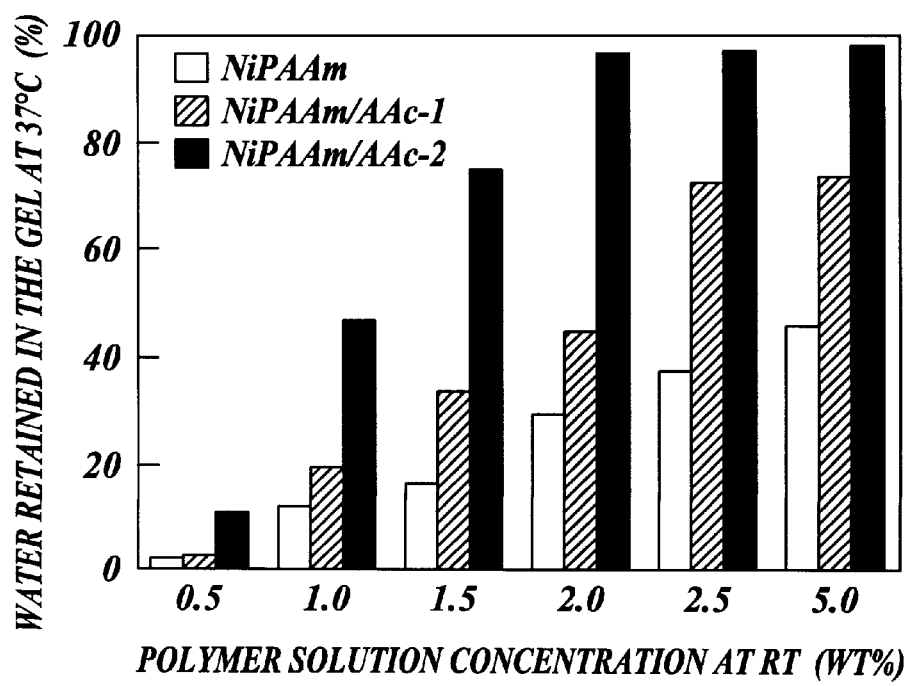
FIG. 2 is a bar graph of water retention in the gel versus initial copolymer concentration in the gelling solution.

Thermally reversible gel formation was studied at 37° C. The freeze dried copolymer was dissolved in phosphate buffered saline (PBS) at different copolymer concentrations (0.5, 1.0, 1.5, 2.0, 2.5, and 5.0 wt %) forming copolymer solutions. The PBS was specifically 0.15M NaCl, 0.01M phosphates $KH_2PO_4$, and $Na_2HPO_4$. The copolymer solutions were thermally equilibrated at 37° C. for 24 hours. The syneresis (amount of water expelled from the gel) was measured gravimetrically. Syneresis of thermoreversible hydrogels of N-isopropylacrylamide (NiPAAm) and its copolymers with acrylic acid (AAc) was affected by copolymer composition (0, 1, 2 mol % of AAc) and polymer concentration as shown in FIG. 2. In FIG. 2 the amount of water retained in the gel is plotted as a function of the initial copolymer concentration in solution (before gelling). It was unexpectedly discovered that the solution containing at least about 2 wt % of the NiPAAm/AAc copolymer having at least about 2.0 mol % of AAc was able to produce a reversible gel exhibiting substantially no syneresis.

EXAMPLE 2

A study was conducted, to demonstrate lack of cytotoxic effect of the gelling cell culture medium on fibroblast cells. A modified ASTM protocol (F 818) was followed for direct contact cytotoxicity tests. The L929 fibroblast cell line was used. Cells were allowed to grow to near confluence (~1 week) in control wells and test wells. A gelling cell culture medium containing a cell culture medium (Minimum Essential Medium (MEM) supplemented with glycine, fetal bovine calf serum and Gentamycine (antibiotic)) and a 2.5 wt % of sterilized NiPAAm/AAc copolymer solution in phosphate buffered saline was placed over the cells in the test wells. For the control wells copolymer was not added to the culture medium. All cells were further incubated for 24 hours.

After 24 hours the gel containing test wells were taken out of the incubator for 5 minutes in order to melt (dissolve) the gelled medium. Dissolved medium was then removed and the wells were washed with a fresh medium. The washing step was also performed for the control wells. The cells were then trypsinized and stained with trypan blue to allow for cell counting using a hemocytometer. The results are summarized in Table E2-1 for the control wells and in Table E2-2 for the test wells. The control and test wells demonstrated comparable cell counts, for both viable and dead cells. Based on these results, it was concluded that the copolymer was not cytotoxic.

TABLE E2-1

Control Well Test Results

|  | Dead Cells | Viable Cells | Viable/mL | # Viable |
|---|---|---|---|---|
| Well 1 | 1 | 644 | 6.44E + 5 | 1.29E + 7 |
| Well 2 | 0 | 504 | 5.04E + 5 | 1.01E + 7 |
| Well 3 | 0 | 485 | 4.85E + 5 | 0.97E + 7 |
| Well 4 | 0 | 525 | 5.25E + 5 | 1.05E + 7 |
| Ave. Wells |  |  |  | 1.08E + 7 |
| Std.Dev. |  |  |  | 0.14E + 7 |

TABLE E2-2

Test Well Test Results

|  | Dead Cells | Viable Cells | Viable/mL | # Viable |
|---|---|---|---|---|
| Well 1 | 3 | 562 | 5.62E + 5 | 1.12E + 7 |
| Well 2 | 0 | 658 | 6.58E + 5 | 1.32E + 7 |
| Well 3 | 0 | 476 | 4.76E + 5 | 0.95E + 7 |
| Well 4 | 0 | 645 | 6.45E + 5 | 1.29E + 7 |
| Ave. Wells |  |  |  | 1.17E + 7 |
| Std.Dev. |  |  |  | 0.17E + 7 |

EXAMPLE 3

An experiment was conducted to demonstrate that making a three dimensional cell matrix according to the present invention and recovering the cells therefrom.

Chondrocites from adult rabbit scapular cartilage were harvested and cultured in a monolayer culture until confluency (about 2 wks). Then, the cells were harvested and seeded into the gelling cell culture medium containing 5 wt % [meth-]acrylamide gel and cultured for 2–3 weeks. The phenotype of the cultured cells was then characterized. To avoid disturbing the association between cells, a slide warmer was used to keep the temperature above 37° C. during the process of media changes.

Two groups of control cultures, monolayer and agarose gel, were used to compare their ability of maintaining chondrocyte phenotype. By the 14 and 21 days, the cells in monolayer culture appeared to be more fibroblast-like. The [meth-]acrylamide polymer and agarose gel cultures reexpressed the chondrocyte phenotype from the first generation of cells obtained from monolayer culture. Large amounts of proeoglycan around large oval or round cells was shown in the agarose gel by the Alcian blue and Safranin O staining. The positive ALP staining showed the existence of ALP in the cell. On the cytospined slides from the cells recovered from the [meth-]acrylamide polymer culture, large oval or round cells were shown by H&E staining and positive ALP staining.

To avoid disturbing the association between cells, a slide warmer was used to keep the temperature above 37° C.

The number of cells doubled in 14 days in the three dimensional cell culture matrix, from $3(10^5)$ cells/ml to $6.6(10^5)$ cells/ml. This indicates that the [meth-]acrylamide polymer culture not only makes the cells regain their chondrocyte phenotype but also promotes cell duplication. Rabbit chondrocyte cells harvested from the 3D matrix after 14 days showed normal morphology and elevated function of matrix production.

In conclusion, the chondrocytes isolated from rabbit scapular cartilage can reexpress their chondrocyte phenotype in three dimensional matrices of agarose culture and [meth-]acrylamide polymer culture but not in the monolayer culture. Also, because the cultured chondrocytes were easily recovered from the [meth-]acrylamide polymer gel culture by simply lowering the temperature, cells may be recovered fully and easily for seeding into a scaffold.

CLOSURE

While a preferred embodiment of the present invention has been shown and described, it will be apparent to those skilled in the art that many changes and modifications may be made without departing from the invention in its broader aspects. The appended claims are therefore intended to cover all such changes and modifications as fall within the true spirit and scope of the invention.

We claim:

1. A gelling cell culture medium, useful for forming a three dimensional matrix for cell culture in vitro, the gelling cell culture medium, comprising:
    (a) a reversible gelling copolymer that is a linear random copolymer of:
        (i) a monomer selected from the group consisting of an acrylamide derivative, a methacrylamide derivative and combinations thereof; and
        (ii) a hydrophilic comonomer different from said monomer in (i);
    said linear random copolymer in the form of a plurality of linear chains having a plurality of molecular weights greater than or equal to a minimum gelling molecular weight cutoff;
    (b) an aqueous solvent mixed with said reversible gelling copolymer as a reversible gelling solution; and
    (c) a cell culture medium mixed with said reversible gelling solution as said gelling cell culture medium.

2. The gelling cell culture medium as recited in claim 1, wherein an amount of said hydrophilic comonomer in the linear random copolymer is less than about 10 mol %.

3. The gelling cell culture medium as recited in claim 2, wherein said amount is about 2 mol %.

4. The gelling cell culture medium as recited in claim 1, wherein said acrylamide derivative is N,N'-alkyl substituted acrylamide.

5. The gelling cell culture medium as recited in claim 4, wherein said N,N'-alkyl substituted acrylamide is selected from the group consisting of N-isopropyl acrylamide, N,N'-diethylacrylamide, N-acryloylpyrrolidine, N-ethylacrylamide, and combinations thereof.

6. The gelling cell culture medium as recited in claim 1, wherein said hydrophilic comonomer is a hydrophilic methacrylic or acrylic compound.

7. The gelling cell culture medium as recited in claim 6, wherein said hydrophilic methacrylic or acrylic compound is selected from the group consisting of carboxylic acid, hydrophilic acrylic acid ester, hydrophilic methacrylic acid ester, hydrophilic acrylamide derivatives, hydrophilic methacrylamide derivatives and combinations thereof.

8. The gelling cell culture medium as recited in claim 7, wherein said carboxylic acid is selected from the group consisting of acrylic acid, methacrylic acid and combinations thereof.

9. The gelling cell culture medium as recited in claim 7, wherein said hydrophilic acrylamide derivatives are selected from the group consisting of N,N-diethylacrylamide, 2-ethylacrylamide, 2-ethylacrylamide, or combinations thereof.

10. The gelling cell culture medium as recited in claim 7, wherein said hydrophilic acrylic acid ester is selected from the group consisting of 2-ethylacrylate, 2-ethylacrylate, and combinations thereof.

11. The gelling cell culture medium as recited in claim 1, wherein said aqueous solvent is selected from the group consisting of water, and aqueous salt solution.

12. The gelling cell culture medium as recited in claim 11, wherein said salt solution is a phosphate buffered saline.

13. The gelling cell culture medium as recited in claim 12, wherein an amount of said solvent is from about 70 wt % to about 99 wt %.

14. The gelling cell culture medium as recited in claim 1, further comprising a plurality of phenotypical cells as a seeded gelling cell culture medium.

15. The gelling cell culture medium as recited in claim 1, wherein said methacrylamide derivative is N,N'-alkyl substituted methacrylamide.

16. The gelling cell culture medium as recited in claim 15, wherein said N,N'-alkyl substituted methacrylamide is selected from the group consisting of N-isopropylmethacrylamide, N,N'-diethylmethacrylamide, N-methacryloylpyrrolidine, N-ethylmethacrylamide, and combinations thereof.

17. The gelling cell culture medium as recited in claim 7, wherein said hydrophilic methacrylamide derivatives are selected from the group consisting of N,N-diethylmethacrylamide, 2-ethylmethacrylamide, 2-ethylmethacrylamide, or combinations thereof.

18. The gelling cell culture medium as recited in claim 7, wherein said hydrophilic methacrylic acid ester is selected from the group consisting of 2-ethylmethacrylate, 2-ethylmethacrylate, and combinations thereof.

19. A method of making a gelling cell culture medium for in vitro cell culturing, comprising the steps of:

(a) mixing a monomer selected from the group consisting of an acrylamide derivative, a methacrylamide derivative and combinations thereof with a hydrophilic comonomer different from said monomer in a reaction solvent with an initiator forming a reaction mixture;

(b) copolymeizing the fraction mixture to form a linear random copolymer having a plurality of linear chains having a plurality of molecular weights;

(c) isolating and purifying the linear random copolymer to obtain a thermally reversible linear random copolymer having a plurality of molecular weights greater than or equal to a minimum gelling molecular weight cutoff;

(d) mixing the thermally reversible copolymer with an aqueous solvent to form a reversible gelling solution; and (e) adding a cell culture medium to said reversible gelling solution to obtain the gelling cell culture medium.

20. The method as recited in claim 19, wherein said initiator is a free radical initiator.

21. The method as recited in claim 19, wherein an amount of said hydrophilic comonomer in the linear random copolymer is less than 10 mol %.

22. The method as recited in claim 21, wherein said amount is about 2 mol %.

23. The method as recited in claim 19, wherein said acrylamide derivative is N,N'-alkyl substituted acrylamide.

24. The method as recited in claim 23, wherein said N,N'-alkyl substituted acrylamide is selected from the group consisting of N-isopropylacrylamide, N,N'-diethylacrylamide, N-acryloylpyrrolidine, N-ethylacrylamide, and combinations thereof.

25. The method as recited in claim 17, wherein said hydrophilic comonomer is a hydrophilic methacrylic or acrylic compound.

26. The method as recited in claim 25, wherein said hydrophilic methacrylic or acrylic compound is selected from the group consisting of carboxylic acid, hydrophilic acrylic acid ester, hydrophilic methacrylic acid ester, hydrophilic acrylamide derivatives, hydrophilic methacrylamide derivatives and combinations thereof.

27. The method as recited in claim 26, wherein said carboxylic acid is selected from the group consisting of acrylic acid, methacrylic acid and combinations thereof.

28. The method as recited in claim 26, wherein said hydrophilic acrylamide derivatives are selected from the group consisting of N,N-diethylacrylamide, 2-ethylacrylamide, 2-ethylacrylamide, or combinations thereof.

29. The method as recited in claim 26, wherein said hydrophilic acrylic acid ester is selected from the group consisting of 2-ethylacrylate, 2-ethylacrylate, and combinations thereof.

30. The method as recited in claim 19, wherein said reaction solvent is selected from the group consisting of aqueous solvent, hydrocarbon solvent, and combinations thereof.

31. The method as recited in claim 30, wherein said aqueous solvent is selected from the group consisting of water, aqueous salt solution and combinations thereof.

32. The method as recited in claim 30, wherein said hydrocarbon solvent is selected from the group consisting of oxygenated hydrocarbon, chlorinated hydrocarbon, aromatic hydrocarbon, and combinations thereof.

33. The method as recited in claim 32, wherein said oxygenated hydrocarbon is dioxane.

34. The method as recited in claim 32, wherein said chlorinated hydrocarbon is chloroform.

35. The method as recited in claim 32, wherein said aromatic hydrocarbon is benzene.

36. The method as recited in claim 19, wherein said aqueous solvent is selected from the group consisting of water, and aqueous salt solution.

37. The method as recited in claim 36, wherein said salt solution is a phosphate buffered saline.

38. The method as recited in claim 19, further comprising adding a plurality of phenotypical cells and obtaining a seeded gelling cell culture medium.

39. The method as recited in claim 19, wherein said methacrylamide derivative is N,N'-alkyl substituted methacrylamide.

40. The method as recited in claim 39, wherein said N,N'-alkyl substituted methacrylamide is selected from the group consisting of N-isopropylmethacrylamide, N,N'-diethylmethacrylamide, N-methacryloylpyrrolidine, N-ethylmethacrylamide, and combinations thereof.

41. The method as recited in claim 26, wherein said hydrophilic methacrylamide derivatives are selected from the group consisting of N,N-diethylmethacrylamide, 2-ethylmethacrylamide, 2-ethylmethacrylamide, or combinations thereof.

42. The method as recited in claim 26, wherein said hydrophilic methacrylic ester is selected from the group consisting of 2-ethylmethacrylate, and combinations thereof.

43. A method of in-vitro propagation of phenotypical cells, comprising the steps of:

(a) mixing a monomer selected from the group consisting of an acrylamide derivative, a methacrylamide derivative and combinations thereof, with a hydrophilic comonomer different from said monomer in a reaction solvent with an initiator forming a reaction mixture;

(b) popolymerizing the reaction mixture to form a linear random copolymer having a plurality of linear chains having a plurality of molecular weights;

(c) isolating and purifying the linear random copolymer to obtain a thermally reversible linear random copolymer having a plurality of molecular weights greater than or equal to a minimum gelling molecular weight cutoff;

(d) mixing the thermally reversible copolymer with an aqueous solvent to form a reversible gelling solution;

(e) adding a cell culture medium to said reversible gelling solution to obtain a gelling cell culture medium;

(f) adding the phenotypical cells to the gelling cell culture medium to form a seeded gelling cell culture medium; and (g) raising a temperature of the seeded gelling cell culture medium to gel the seeded gelling cell culture medium to form a gelled culture medium.

44. The method as recited in claim 43, further comprising the step of:

recovering the phenotypical cells from the gelled culture medium by lowering the temperature and dissolving the gelled culture medium.

45. The method as recited in claim 44, further comprising the step of:

recovering the phenotypical cells from the gelled culture medium by lowering the temperature and dissolving the gelled culture medium.

46. The method as recited in claim 43, wherein an amount of said linear random copolymer in the gelling cell culture medium is less than 20 wt %.

47. The method as recited in claim 46, wherein said amount is less than 5 wt %.

* * * * *